United States Patent [19]

Kikuchi et al.

[11] 4,374,477
[45] Feb. 22, 1983

[54] ULTRASONIC MEASURING DEVICE

[75] Inventors: Akira Kikuchi; Akio Hagiya, both of Tokyo; Kazuteru Shinkai; Masaru Kohno, both of Kawasaki; Kiyoshi Saito, Tachikawa all of Japan

[73] Assignee: Fuji Electric Co., Ltd., Kanagawa, Japan

[21] Appl. No.: 247,032

[22] Filed: Mar. 24, 1981

[30] Foreign Application Priority Data

Mar. 25, 1980 [JP] Japan .................. 55-37844

[51] Int. Cl.³ .................................... G01F 1/66
[52] U.S. Cl. .................. 73/861.18; 73/861.27; 310/346
[58] Field of Search ........... 73/632, 644, 861.18, 73/861.25, 861.26, 861.27, 861.28; 310/341, 342, 344, 346

[56] References Cited

U.S. PATENT DOCUMENTS

| | | | |
|---|---|---|---|
| 3,242,723 | 3/1966 | Evans | 310/341 X |
| 3,935,484 | 1/1976 | Leschek et al. | 310/346 X |
| 4,019,373 | 4/1977 | Freeman et al. | 73/644 X |
| 4,098,117 | 7/1978 | Baumoel | 73/861.27 X |
| 4,286,470 | 9/1981 | Lynnworth | 73/861.18 |

Primary Examiner—Charles A. Ruehl
Attorney, Agent, or Firm—Sughrue, Mion, Zinn, Macpeak and Seas

[57] ABSTRACT

An ultrasonic measuring device for measuring the fluid flow of a high temperature fluid in a conduit. Ultrasonic transducers are mounted on first and second frames which have end portions hingedly coupled to one another. A tightening device at the other ends of the frames are used to secure the frames around the conduit carrying the fluid to be measured. Lead wires extend through hollow pipes between the ultrasonic transducers and connecting terminals at the outward ends thereof. Heat radiating fins may be provided at the outward ends of the pipes. With this construction, the outward ends of the pipes are at room temperature so that ordinary coaxial cables may be joined to the connecting terminals.

6 Claims, 5 Drawing Figures

ULTRASONIC MEASURING DEVICE

BACKGROUND OF THE INVENTION

The present invention relates to an ultrasonic measuring device in which two ultrasonic transducers are arranged on both sides of a pipe in which a fluid to be measured flows, one of the ultrasonic transducers transmits an ultrasonic wave towards and through the fluid, and the other ultrasonic transducer receives the ultrasonic wave which has passed through the fluid.

As shown in FIG. 1, an ultrasonic measuring device such as an ultrasonic flow meter has two detectors (or ultrasonic transducers) D and D'. The detectors D and D' are arranged on the upstream side and the downstream side of a flow of fluid to be measured and the ultrasonic wave is propagated as indicated in the figure. The flow rate of the fluid is measured utilizing the fact that there is a time difference between a period of time $t_1$ required for the ultrasonic wave to propagate from the upstream side to the downstream side and a period of time $t_2$ required for it to propagate from the downstream side to the upstream side when the fluid is flowing and the magnitude of the difference is related to the flow rate of the fluid.

FIG. 2 is a perspective view of a conventional ultrasonic measuring device of this general type. In FIG. 2, reference numeral 1 designates a pipe in which a fluid at high temperature to be measured flows. An upstream detector 3 and a downstream detector 4 are mounted on opposite sides of the pipe 1, and the detection signals of the detectors are transmitted to a measuring circuit which is located remotely therefrom. For this purpose, coaxial cables which are designed to be used at room temperature are employed. However, since the heat resisting temperature of typical coaxial cables is limited to 100° C. or lower, heat resistant wires 6 and 7 such as MI cables are used in the vicinity of the pipe 1 which is at a high temperature, for instance, 100° C. to 500° C. The heat resistant cable 6 or 7 is covered with a metal sheath. Therefore, it has a low flexibility, and it is heavy and expensive. Accordingly, the cables 6 and 7 are used only in limited lengths. A relay terminal box 8 is set at a place where the ambient temperature is not affected by the high temperature of the pipe 1. The ends of the heat resistant cables 6 and 7 are connected to the relay terminal box 8 from which ordinary coaxial cables 9 and 10 extend to a measuring circuit (not shown).

The metal sheath of the above-described heat resistant cable 6 or 7 is filled with insulating powder such as alumina. Therefore, it has a low flexibility, is rigid and heavy. Accordingly, the heat resistant cable suffers from the following difficulties: (a) Because of its low flexibility, wiring work with the cable is difficult. (b) If after being coupled to the frame of the detector during manufacturing the heat resistant cable is shipped, its package is bulky and is not suitable for transportation. (c) If, during installation or removal or during the maintenance and inspection the heat resistant cable is accidentally called by the operator's foot, for instance, the connection to the detector is liable to be damaged because of the rigidity of the cable. (d) Since the heat resistant cable has a low flexibility and is expensive, it is not suitable for use over long distances. Accordingly, the length of the heat resistant cable is limited, and the heat resistant cable must be coupled through an ordinary cable to the measuring circuit. For this purpose, it is necessary to provide a relay terminal box.

With an ultrasonic flow meter of this type, the flow rate of a fluid flowing in a pipe can be measured merely by mounting the detectors on the pipe. That is, it is unnecessary to bring the detectors directly into contact with the fluid to measure the flow rate. Accordingly, the ultrasonic flow meter is advantageous in that it can be used with a pipe after the pipe has been installed. Therefore, the detectors are often mounted on pipes and removed therefrom in a plant. However, the working temperatures in such situations are often very high or the working area may be contaminated with radiation making it dangerous to use the detectors. Accordingly, it is required that the ultrasonic measuring device meet the following requirements: (a) The construction thereof must be such that the device can be mounted on and removed from a pipe quickly with no intricate adjustment. (b) The construction must be such that the maintenance of the device can be easily performed. (c) In the case where a fluid to be measured is at high temperature (100°–500° C.) or it is at extremely low temperature (as in the case of liquid nitrogen or liquid hydrogen), the operator must not be exposed to the high temperature or extremely low temperature when he connects or disconnects the lead wires of the ultrasonic transducers.

Accordingly, an object of the invention is to provide an ultrasonic measuring device in which the above-described difficulties accompanying a conventional ultrasonic measuring device and which satisfies all the above-described requirements.

SUMMARY OF THE INVENTION

In accordance with this and other objects of the invention, there is provided an ultrasonic measuring device including two ultrasonic transducers adapted to be arranged on opposite sides of a pipe in which a fluid to be measured flows. A first of the ultrasonic transducers transmits an ultrasonic wave towards and through the fluid while the second of the ultrasonic transducers receives the ultrasonic waves which have passed through the fluid. A first frame is provided for holding the first ultrasonic transducer and a second frame for holding the second ultrasonic transducer. The first and second frames have first end portions which are hingedly coupled together so that the first and second frames clamp the pipe. Tightening means is provided for rigidly securing the free end portions of the first and second frames. First and second hollow pipes are secured to the first and second frames extending outwardly therefrom substantially parallel to one another. Connecting terminals are provided at the outward ends of the first and second hollow pipes away from the frames. Lead wires are connected to the ultrasonic transducers and extend through the hollow pipes at ends of which the connecting terminals are provided. A heat radiating fin may be provided adjacent to the connecting terminals on each of the hollow pipes.

DESCRIPTION OF THE PREFERRED EMBODIMENTS

Figure 1:
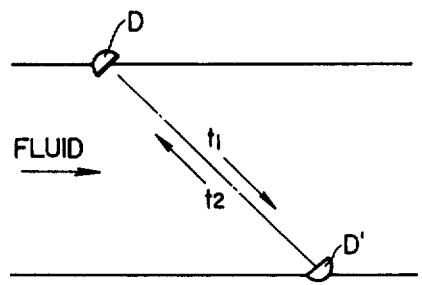
FIG. 1 is an explanatory diagram for a description of the principle of an ultrasonic flow meter.
Figure 5:
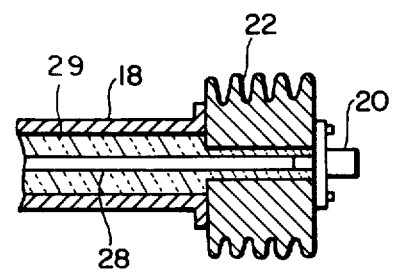
FIG. 5 is a sectional view of parts of the ultrasonic flow meter in FIG. 3.
Figure 3:
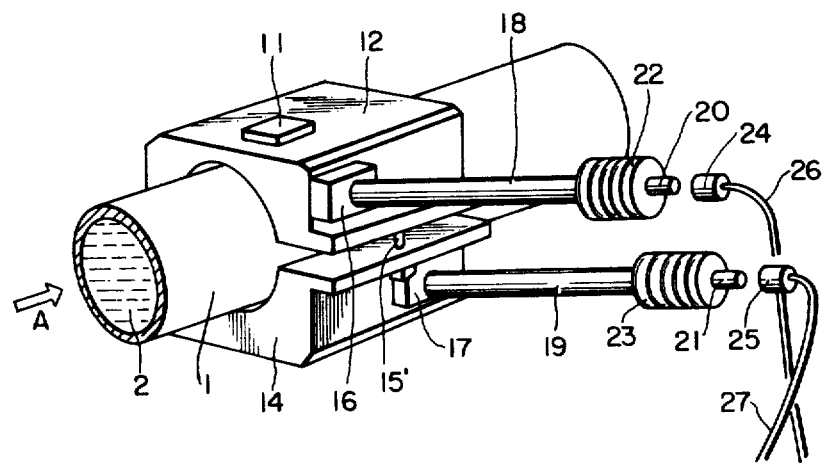
FIG. 3 is a perspective view of a preferred embodiment of an ultrasonic flow meter according to the invention.
Figure 4:
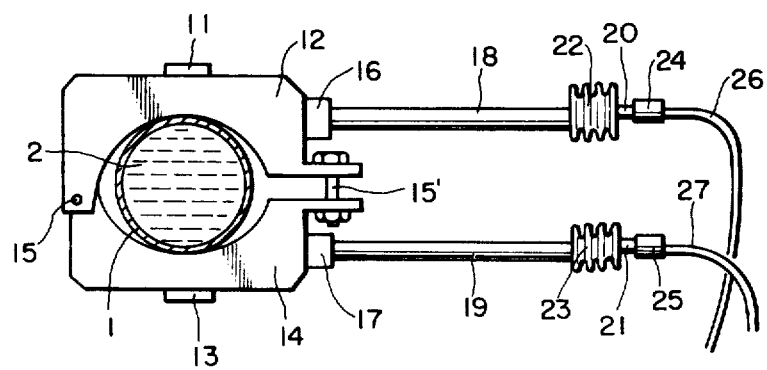
FIG. 4 is a diagram showing the ultrasonic flow meter of FIG. 3 as viewed in the direction of the arrow A in FIG. 3.

A preferred embodiment of an ultrasonic measuring device according to the invention will be described with reference to FIGS. 3, 4 and 5. FIG. 3 is a perspective view of the ultrasonic measuring device. FIG. 4 is a diagram of the ultrasonic measuring device as viewed along an arrow in FIG. 3. FIG. 5 is a sectional view of essential components of the ultrasonic measuring device shown in FIG. 3.

Referring to these figures, a fluid 2 to be measured flows in a pipe 1. One end portion of a frame 12 holding an upstream detector 11 is hinged to one end portion of a frame 14 holding a downstream detector 13. The frames 12 and 14 are mounted on the pipe 1 in such a manner that they clamp the pipe 1, and the frames are fixedly secured to the pipe 1 by tightening the other end portions thereof with a tightening metal fixture 15'. The frames 12 and 14 are provided with pipe mounting seats 16 and 17, respectively. Hollow pipes (such as stainless steel pipes) 18 and 19 are fixedly secured to the mounting seats 16 and 17 by threadedly engaging them with the seats or by any other suitable method. If necessary, heat-insulating material 29 may be filled in the hollow pipes 18 and 19.

Furthermore, lead wires 28 connected to the detectors 11 and 13 are inserted into the hollow pipes 18 and 19 and are connected to connecting terminals (receptacles) 20 and 21 provided at the outer ends of the hollow pipes 18 and 19, respectively. If necessary, heat radiating fins 22 and 22 may be provided on the outer end portions of the hollow pipes 18 and 19 adjacent the receptacles 20 and 21, respectively. In FIGS. 3 and 4, reference numerals 24 and 25 designate mating connecting terminals (plugs) for the connecting terminals 20 and 21, respectively. The mating connecting terminals 24 and 25 are connected to coaxial cables 26 and 27, respectively. When the receptacles 20 and 21 are coupled to the plugs 24 and 25, signals from the detectors 11 and 13 are transmitted through the lead wires 28, the connecting terminals 20, 21, 24 and 25 and the coaxial cables 26 and 27 to a control circuit.

Each of the hollow pipes is made of a heat resistant material which is selected to have as low a thermal conductivity as possible that it has a large temperature gradient in the axial direction thereof, whereby even if the temperature of the pipe 1 is high, the connecting terminals 20, 21, 24 and 25 are substantially at room temperature. The heat radiating fins are provided in order to cause the temperatures of the connecting terminals 20, 21, 24 and 25 to further approach room temperature. The connecting terminal (receptacle) 20 can be connected to the mating connecting terminal (plug) 24 by one action as can the other connecting terminal (receptacle) 21 can be connected to the other mating connecting terminal (plug) 25. Therefore, the operations of connecting and laying the cables can be readily achieved.

While the invention has been described with reference to the case where the fluid to be measured is at a high temperature, the technical concept of the invention is applicable to the case where the fluid is at a low temperature. The latter case is different from the former case only in that the hollow pipes are made of a cold-proof material and the heat radiating fins serve as heat collecting means.

With the ultrasonic measuring device according to the invention is constructed as described above, the coaxial cables are not affected by the high or low temperature of the pipe in which the fluid to be measured flows. Accordingly, the coaxial cables can be readily connected to or disconnected from the device and the maintenance of the coaxial cables is much improved.

An actual example of an ultrasonic measuring device of the invention was assembled to perform various experiments. According to the results of the experiments, only about one minute was required for mounting the detectors and the frames on a pipe. Also, it took only ten seconds or less to connect the connecting terminals electrically coupled to the detectors to the mating connecting terminals of the coaxial cables. Thus, the working efficiency in a plant can be significantly improved. Hollow stainless steel pipes 15 cm in diameter were employed as the hollow pipes 18 and 19. In this case, when the temperature of the pipe 1 and the frames 12 and 14 was 300° C., the connecting terminals 20 and 21 were at room temperature. That is, in the hollow pipes 18 and 19, a temperature of 300° C. was decreased to room temperature.

The essential points of the invention described above are as follows:

(1) In the device of the invention, one end portion of the frame 12 holding one ultrasonic transducer (or one detector 11) is hinged to one end portion of the frame 14 holding the other ultrasonic transducer (or the other detector 13) with the hinge pin 15. After the frames 12 and 14 are mounted on the pipe 1 clamping the pipe 1, the other free end portions of the frames 12 and 14 are tightened with the tightening device (the tightening metal fixture 15). Therefore, the device can be quickly mounted on or removed from a pipe and no intricate adjacent is required. Thus, the working efficiency is improved and maintenance can be readily achieved.

Figure 2:
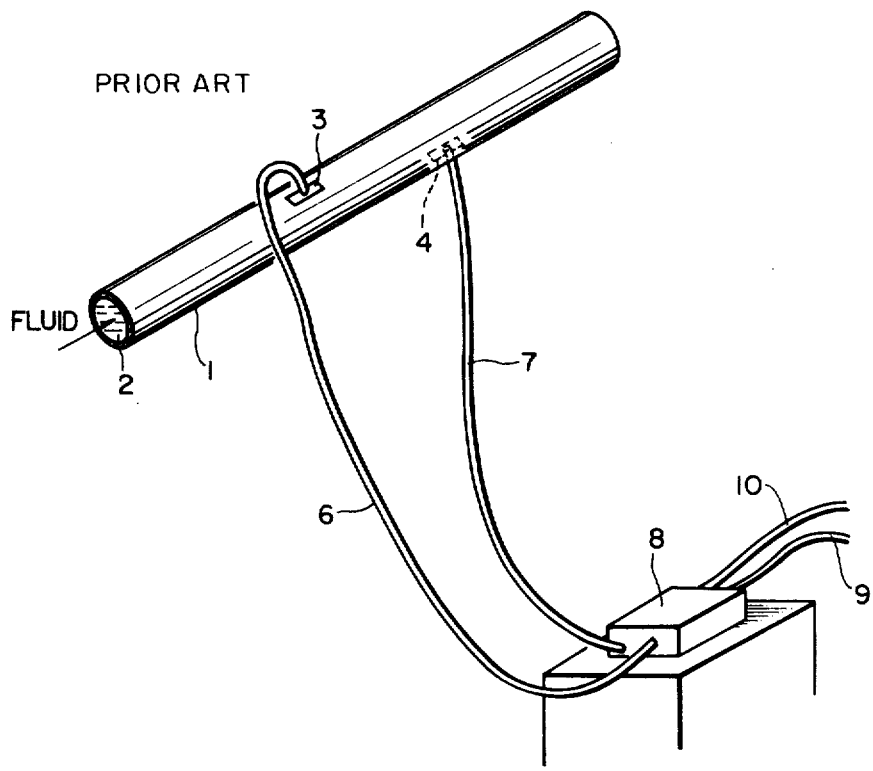
FIG. 2 is a perspective view showing a conventional ultrasonic flow meter.

(2) In the device of the invention, the lead wires of the ultrasonic transducers are inserted into the hollow pipes which are fixedly secured to the frames 12 and 14. The lead wires thus inserted are connected to the connecting terminals 20 and 21 provided at the ends of the hollow pipes 18 and 19, respectively. Accordingly, as heat is conducted from the frames through the hollow pipes to the connecting terminals, the temperature is greatly decreased. Therefore, even a fluid to be measured is at a high temperature, for instance, 100° C. to 500° C., the connecting terminals are maintained at room temperature. As the length of each heat resistant wire can be made substantially equal to the length of the corresponding hollow pipe, the difficulties accompanying the conventional device shown in FIG. 2 are eliminated.

What is claimed is:

1. An ultrasonic measuring device comprising: two ultrasonic transducers arranged on opposite sides of a pipe in which a fluid to be measured flows, a first of said ultrasonic transducers transmitting an ultrasonic wave towards said fluid and a second of said ultrasonic transducer receiving said ultrasonic wave which has passed through said fluid; a first frame holding said first ultrasonic transducer; a second frame having an end portion holding said second ultrasonic transducer, said first and second frames having end portions hingedly coupled to one another and said first and second frames being mounted on said pipe with said first and second frames clamping said pipe; tightening means for tightening free end portions of said first and second frames together; first and second hollow pipes secured to said first and second frames, respectively; first and second connecting terminals mounted at ends of said first and second hollow pipes, respectively, away from said frames; and lead wires connected at first ends to said two ultrasonic transducers, one of said lead wires being disposed in each of said hollow pipes and being connected at second ends to said connecting terminals.

2. The ultrasonic measuring device as claimed in claim 1 further comprising a heat radiating fin adjacent to said connecting terminal on each of said hollow pipes.

3. The ultrasonic measuring device as claimed in claim 1 wherein said hollow pipes are formed of a material having a high thermal conductivity.

4. The ultrasonic measuring device as claimed in claim 1 wherein said hollow pipes are made of stainless steel.

5. The ultrasonic measuring device of claim 1 further comprising first and second mounting seats for mounting said first and second hollow pipes, respectively, to said first and second frames.

6. The ultrasonic measuring device of claim 1 further comprising heat insulating material filled in said hollow pipes.

* * * * *